(12) United States Patent
Iwakami et al.

(10) Patent No.: US 8,119,625 B2
(45) Date of Patent: Feb. 21, 2012

(54) NEUROGENESIS INDUCER OR NEUROPATHY THERAPEUTIC AGENT COMPRISING ALKYL ETHER DERIVATIVE OR SALT THEREOF

(75) Inventors: Noboru Iwakami, Toyama (JP); Shigeki Marubuchi, Toyama (JP); Tomohiro Okuda, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 291 days.

(21) Appl. No.: 12/370,736

(22) Filed: Feb. 13, 2009

(65) Prior Publication Data
US 2009/0209512 A1 Aug. 20, 2009

Related U.S. Application Data

(63) Continuation-in-part of application No. 12/298,656, filed as application No. PCT/JP2007/058841 on Apr. 24, 2007.

(30) Foreign Application Priority Data

Apr. 26, 2006 (JP) .................................. 2006-122080

(51) Int. Cl.
A61K 31/397 (2006.01)
C07D 205/04 (2006.01)
(52) U.S. Cl. ............... 514/210.19; 548/952; 514/210.01
(58) Field of Classification Search .................. 548/950, 548/952; 514/210.01, 210.19
See application file for complete search history.

(56) References Cited

U.S. PATENT DOCUMENTS

| 6,294,346 B1 | 9/2001 | Weiss et al. | |
|---|---|---|---|
| 6,797,726 B1 | 9/2004 | Ono et al. | |
| 7,087,594 B2 | 8/2006 | Saitoh et al. | |
| 7,342,043 B2 * | 3/2008 | Nakada et al. ................. | 514/443 |
| 7,468,443 B2 | 12/2008 | Saitoh et al. | |
| 7,834,053 B2 * | 11/2010 | Nakada et al. ................. | 514/443 |
| 2004/0030131 A1 | 2/2004 | Keenan et al. | |
| 2004/0167171 A1 | 8/2004 | Ohkawa et al. | |
| 2005/0070521 A1 | 3/2005 | Saitoh et al. | |
| 2006/0194781 A1 | 8/2006 | Saitoh et al. | |
| 2006/0205709 A1 | 9/2006 | Kimura et al. | |
| 2008/0103126 A1 | 5/2008 | Nakada et al. | |

FOREIGN PATENT DOCUMENTS

| EP | 1 437 353 A1 | 7/2004 |
|---|---|---|
| EP | 1 614 419 A1 | 1/2006 |
| JP | 2002 322058 | 11/2002 |
| JP | 2003 81959 | 3/2003 |
| JP | 2004 510754 | 4/2004 |
| WO | 99 31056 | 6/1999 |
| WO | 03 035647 | 5/2003 |

OTHER PUBLICATIONS

Saitoh et al (2003): STN International HCAPLUS database, (Columbus, Ohio), Accession No. 2003:335103.*

Santarelli, Luca et al., "Requirement of Hippocampal Neurogenesis for the Behavioral Effects of Antidepressants", Science, vol. 301, pp. 805-809, (2003).
Sugaya, K.,"Neuroreplacement therapy and stem cell biology under disease conditions", CMLS Cellular and Molecular Life Sciences, vol. 60, pp. 1891-1902, (2003).
Tohru, Michio et al., "ICD-10 Seishin oyobi koudou no syougai—Rinshou kijutu to sindan gaidorain—Shinteiban (ICD-10 mental and behavioral disorder—clinical description and diagnosis guidelines—a newly revised edition)", Igaku-Shoin, pp. 23-49, 2005, (with English translation).
Shah, Premal J. et al., "Cortical grey matter reductions associated with treatment-resistant chronic unipolar depression", British Journal of Psychiatry, vol. 172, pp. 527-532, (1998).
Bogerts, Bernhard et al., "Hippocampus-Amygdala Volumes and Psychopathology in Chronic Schizophrenia", Biol Psychiatry, vol. 33, No. 4, pp. 236-246, (1993).
Gurvits, Tamara V. et al., "Magnetic Resonance Imaging Study of Hippocampal volume in Chronic, Combat-Related Posttraumatic Stress Disorder", Biol Psychiatry, vol. 40, No. 11, pp. 1091-1099, (1996).
Harrison, Paul J., "The neuropathology of primary mood disorder", Brain, vol. 125, pp. 1428-1449, (2002).
Eriksson, Peter S. et al., "Neurogenesis in the adult human hippocampus", Nature Medicine, vol. 4, No. 11, pp. 1313-1317, (1998).
Wakade, Chandramohan G. et al., "Atypical Neuroleptics Stimulate Neurogenesis in Adult Rat Brain", Journal of Neuroscience Research, vol. 69, No. 1, pp. 72-79, (2002).
U.S. Appl. No. 12/683,813, filed Jan. 7, 2010, Nakada, et al.
U.S. Appl. No. 12/253,379, filed Oct. 17, 2008, Saitoh, et al.

(Continued)

*Primary Examiner* — Golam M M Shameem
(74) *Attorney, Agent, or Firm* — Oblon, Spivak, McClelland, Maier & Neustadt, L.L.P.

(57) ABSTRACT

Disclosed is an agent comprising a benzothiophene alkyl ether derivative represented by the general formula below or a salt thereof:

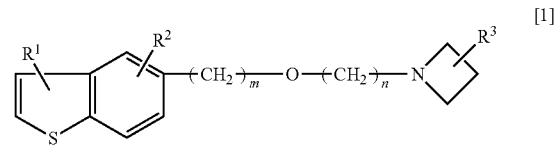

[1]

wherein $R^1$ and $R^2$ independently represent at least one group selected from a hydrogen atom, a halogen atom, an alkyl group, an aryl group, an aralkyl group, an alkoxy group, an aryloxy group, an alkylthio group, an arylthio group, an alkenyl group, an alkenyloxy group, an amino group, an alkylsulfonyl group, an arylsulfonyl group, a carbamoyl group, a heterocyclic group, an amino group, a hydroxyl group, a carboxyl group, a nitro group, an oxo group and the like; $R^3$ represents an alkylamino group which may be substituted or an amino or hydroxyl group which may be protected; and m and n independently represent an integer ranging from 1 to 6. The agent is useful as a neurogenesis inducer or a therapeutic agent for neuropathy.

19 Claims, No Drawings

OTHER PUBLICATIONS

Kazunari Hirata, et al., "A Novel Neurotrophic Agent, T-817MA [1-{3-[2-(1-Benzothiophen-5-yl) Ethoxy] Propyl}-3-azetidinol Maleate], Attenuates Amyloid-β-induced Neurotoxicity and Promotes Neurite Outgrowth in Rat Cultured Central Nervous System Neurons", The Journal of Pharmacology and Experimental Therapeutics, vol. 314, No. 1, 2005, pp. 252-259.

Tetsuo Fukushima, et al., "T-817MA, a novel neurotrophic agent, improves sodium nitroprusside-induced mitochondrial dysfunction in cortical neurons", Neurochemistry International, vol. 48, 2006, pp. 124-130.

Phuong Thi Hong Nguyen, et al., "Ameliorative Effects of a Neuroprotective Agent, T-817MA, on Place Learning Deficits Induced by Continuos infusion of Amyloid-β Peptide (1-40) in Rats", Hippocampus, vol. 17, No. 6, 2007, pp. 443-455.

N. Wakami, et al., "T-817MA, a neurotrophic compound, delays progression of motor deficits and neuronal death in transgenic mice expressing P301L mutant tau protein", 33$^{rd}$ Annual Meeting Society for Neuroscience, Nov. 8-12, 2003, 1 page.

Y. Nakada, et al., "T-817MA, a neurotrophic compound, protects neurodegeneration in rats with continuous infusion of amyloid-β peptide", 33$^{rd}$ Annual Meeting Society for Neuroscience, Nov. 8-12, 2003, 1 page.

H. Yamaguchi, et al., "T-817MA, a neurotrophic compound, reverses Aβ neurotoxicity and promotes neurite 97.5 outgrowth through P13-kinase pathway in rat primary cultured neurons.", 33$^{rd}$ Annual Meeting Society for Neuroscience, Nov. 8-12, 2003, 1 page.

K. Hirata, et al., "T-588 and T-817MA, neuroprotective agents, decrease High K+-induced necrotic damages of Purkinje cells in cerebellum organotypic slice culture.", 33$^{rd}$ Annual Meeting Society for Neuroscience, Nov. 8, 2003, 1 page.

Y. Nakada, et al., "T-817MA, A Neurotrophic agent, improves declined cognition caused by continuous infusion of amyloid-β peptide in rats", 34$^{th}$ Annual Meeting Society for Neuroscience, Oct. 23-27, 2004, 1 page.

Tetsuo Fukushima, et al., T-817MA, a neurotrophic compound, protects against sodium nitroprusside-induced toxicity in rat primary cultured neurons, 78$^{th}$ Annual Meeting of the Japanese Pharmacological Society, Mar. 23, 2005, 1 page.

N. Iwakami, et al., "T-817MA, a newly developing anti-Alzheimer agent, protects neurons and recovers memory in amyloid β-infused rats and P301L tau-mutated mice", Alzheimer's Association International Conference on Prevention of Dementia, Jun. 18-21, 2005, 2 pages.

Tatsuo Kimura, et al., "T-817MA, neuroprotective agent, ameliorates place learning deficits induced by continuos infusion of amyloid-β peptide in rats", 35$^{th}$ Annual Meeting Society for Neuroscience, Nov. 12-16, 2005, 1 page.

Yusaku Takamura, et al., "Antioxidant capacity is a key determinant of cell well-being", 35$^{th}$ Annual Meeting Society for Neuroscience, Nov. 12-16, 2005, 1 page.

Tatsuo Kimura, et al., "Effects of T-817MA on adult neurogenesis and spatial memory in amyloid-β peptide infused rats", 36$^{th}$ Annual Meeting Society for Neuroscience, Oct. 14-18, 2006, 1 page.

T. Fukushima, et al., "T-817MA, A Neurotrophic Compound, Exerts Neuroprotection through Protein Kinase C-dependent Pathway in Rat Primary Cultured Neurons", 36$^{th}$ Annual Meeting Society for Neuroscience, Oct. 14-18, 2006, 1 page.

Yusaku Takamura, et al., "PKCε translocation in primary neuronal cultures is modified by T-817MA: Dynamic real time imaging", 36$^{th}$ Annual Meeting Society for Neuroscience, Oct. 15, 2006, 1 page.

Office Action mailed Jan. 24, 2011, in co-pending U.S. Appl. No. 12/298,656.

* cited by examiner

NEUROGENESIS INDUCER OR NEUROPATHY THERAPEUTIC AGENT COMPRISING ALKYL ETHER DERIVATIVE OR SALT THEREOF

REFERENCE TO RELATED APPLICATIONS

This application is a continuation-in-part of U.S. application Ser. No. 12/298,656, filed Oct. 27, 2008, which is a national-stage filing under S371 of PCT/JP2007/058841, filed Apr. 24, 2007, both of which are hereby incorporated by reference in their entireties. The foreign priority document, JAPAN 2006-122080, filed Apr. 26, 2006, is also incorporated by reference in its entirety. The patent or non-patent documents or publications described in the following disclosure are also incorporated by reference in their entireties, especially with respect to the particular subject matter in these documents or publications to which the disclosure specifically refers.

TECHNICAL FIELD

The present invention relates to an excellent neurogenesis inducer and mental disorder therapeutic agent containing an alkyl ether derivative or a salt thereof.

BACKGROUND ART

As mental disorders, schizophrenia, bipolar emotional disorder, recurrent depressive disorder, phobic anxiety disorder, and the like are known (Non-Patent Document 1). Currently, antipsychotic drugs, antidepressant drugs, antianxiety drugs and the like have been used clinically to treat these mental disorders. There is a need, however, for a drug with increased efficacy and fewer adverse drug reactions.

For example, many of the antipsychotic drugs are dopamine receptor blockers, and may induce extrapyramidal symptoms. Besides, the effect of these drugs to improve negative symptoms is insufficient. It is known for antidepressant drugs that about several weeks are required to manifest their therapeutic effect, some patients are resistant to their therapy, and the remission rate after their therapy is 50% or less. Many antidepressant drugs are known to be addictive and have adverse effects such as drowsiness.

On the other hand, a decreased local brain volume has been reported in various pathological conditions, such as depression, schizophrenia, and mood disorder. A decreased number of brain neurons observed in mental disorders is thought to be closely associated with these pathological conditions of these diseases (Non-Patent Documents 2-5).

Recently, it has been revealed that neurons are generated through proliferation and differentiation of neural stem cells and neural progenitor cells existing in the adult brain (Non-Patent Document 6), and the possibility is indicated that activation and differentiation of endogenous neural stem cells and/or neural progenitor cells will reconstruct the nerve tissue and function reduced in various disorders.

Furthermore, based on the fact that antidepressant drugs, antipsychotic drugs and the like actually exhibit a neurogenesis inducing effect, it is indicated that focusing on the neurogenesis inducing effect will lead to the development of more effective mental disorder therapeutic agents (Non-Patent Documents 7 and 8).

Compounds that induce proliferation and differentiation of the neural stem cells and/or the neural progenitor cells are considered useful as mental disorder therapeutic agents due to their effect of reconstructing the nerve tissue and function reduced in various disorders (Patent Document 2).

To date, alkyl ether derivatives have been reported to have effects of neuroprotection, nerve regeneration, and neurite outgrowth promotion (Patent Document 1). However, their neurogenesis inducing effect has not been known at all.

Patent Document 1: WO 03/035647 pamphlet
Patent Document 2: U.S. Pat. No. 6,294,346 specification
Non-Patent Document 1: Michio Tohru, Yoshibumi Nakane, Minoru Komiyama, Yuuji Okazaki, Yoshirou Ohkubo, "ICD-10 Seishin oyobi koudou no syougai-Rinshou kijutu to sindan gaidorain-Shinteiban (ICD-10 mental and behavioral disorder-clinical description and diagnosis guidelines—a newly revised edition)", Igaku-Shoin, November, 2005, p. 23-49
Non-Patent Document 2: Br. J. Psychiatry., 1988, 172: p. 527-532
Non-Patent Document 3: Biol. Psychiatry., 1993, 33(4): p. 236-246
Non-Patent Document 4: Biol. Psychiatry., 1996, 40(11): p. 1091-1099
Non-Patent Document 5: Brain, 2002, 125: p. 1428-1449
Non-Patent Document 6: Nat. Med., 1998, 11: p. 1313-1317
Non-Patent Document 7: Science, 2003, 301: p. 805-809
Non-Patent Document 8: J. Neurosci. Res., 2002, 69(1): p. 72-79

DISCLOSURE OF THE INVENTION

There is a need for a compound that exhibits a neurogenesis inducing effect and is useful as a neurogenesis inducer and a mental disorder therapeutic agent.

Under such circumstances, the present inventors have found that a benzothiophene alkyl ether derivative represented by a general formula [1]:

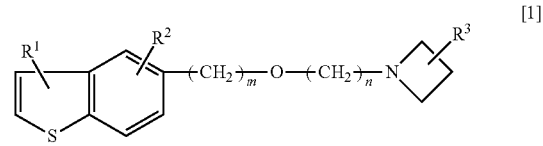

wherein, $R^1$ and $R^2$, which are identical or different, represent one or more group selected from a hydrogen atom, a halogen atom, an optionally substituted alkyl, aryl, aralkyl, alkoxy, aryloxy, alkylthio, arylthio, alkenyl, alkenyloxy, amino, alkylsulfonyl, arylsulfonyl, carbamoyl or heterocyclic group, an optionally protected amino, hydroxyl or carboxyl group, a nitro group and an oxo group;
$R^3$ represents an optionally substituted alkylamino group; or an optionally protected amino or hydroxyl group; and
m and n, which are identical or different, represent integer from 1 to 6 or a salt thereof, has a neurogenesis inducing effect and is therefore useful as a neurogenesis inducer and a mental disorder therapeutic agent, and have completed the present invention.

The alkyl ether derivative represented by the general formula [1] or the salt thereof of the present invention exhibits a neurogenesis inducing effect and is useful as a neurogenesis inducer and a mental disorder therapeutic agent.

BEST MODE FOR CARRYING OUT THE INVENTION

The present invention will now be illustrated in detail below.

Each term in this specification has the following meanings unless otherwise indicated.

A halogen atom means a fluorine atom, a chlorine atom, a bromine atom or an iodine atom; an alkyl group means a linear or branched chain $C_{1-12}$ alkyl group, such as methyl, ethyl, propyl, isopropyl, butyl, isobutyl, tert-butyl, pentyl, hexyl, heptyl and octyl groups; a lower alkyl group means a linear or branched chain $C_{1-6}$ alkyl group, such as methyl, ethyl, propyl, isopropyl, butyl, isobutyl, tert-butyl, pentyl and hexyl groups; a alkenyl group means a $C_{2-12}$ alkenyl group, such as vinyl, propenyl, butenyl, pentenyl, hexenyl, heptenyl and octenyl; a lower alkenyl group means a $C_{2-6}$ alkenyl group, such as vinyl, propenyl, butenyl, pentenyl and hexenyl; an acylalkyl group means, for example, such a group as acetylmethyl, benzoylmethyl, p-nitrobenzoylmethyl, p-bromobenzoylmethyl, p-methoxybenzoylmethyl and 1-benzoylethyl; an acyloxyalkyl group means, for example, such a group as acetoxymethyl, propionyloxymethyl and pivaloyloxymethyl; an arylthioalkyl group means, for example, such a group as phenylsulfenylmethyl and 2-(p-nitrophenylsulfenyl)ethyl; an arylsulfonylalkyl group means, for example, such a group as p-toluenesulfonylethyl; a nitrogen-containing heterocyclic alkyl group means, for example, such a group as phthalimidomethyl and succinimidomethyl; a cycloalkyl group means, for example, a $C_{3-8}$ cycloalkyl group, such as cyclopropyl, cyclobutyl, cyclopentyl and cyclohexyl; an alkylthioalkyl group means, for example, a $C_{1-6}$ alkylthio-$C_{1-6}$ alkyl group, such as methylthiomethyl, ethylthiomethyl and propylthiomethyl; an alkoxyalkyl group means, for example, a $C_{1-6}$ alkyloxy-$C_{1-6}$ alkyl group, such as methoxymethyl and 1-ethoxyethyl; an aralkyloxyalkyl group means, for example, an ar-$C_{1-6}$ alkyloxy-$C_{1-6}$ alkyl group, such as benzyloxymethyl and phenethyloxymethyl.

An alkoxy group means a linear or branched chain $C_{1-12}$ alkyloxy groups, such as methoxy, ethoxy, propoxy, isopropoxy, butoxy, isobutoxy, tert-butoxy, pentyloxy, hexyloxy, heptyloxy and octyloxy groups; a lower alkoxy group means a linear or branched chain $C_{1-6}$ alkyloxy groups, such as methoxy, ethoxy, propoxy, isopropoxy, butoxy, isobutoxy, tert-butoxy, pentyloxy and hexyloxy groups; an alkenyloxy group means a $C_{2-12}$ alkenyloxy group, such as vinyloxy, propenyloxy, butenyloxy, pentenyloxy, hexenyloxy, heptenyloxy and octenyloxy groups.

An alkylthio group means a $C_{1-12}$ alkylthio group, such as methylthio, ethylthio, propylthio, isopropylthio, butylthio, isobutylthio, tert-butylthio, pentylthio, hexylthio, heptylthio and octylthio; a lower alkylthio group means a $C_{1-6}$ alkylthio groups, such as methylthio, ethylthio, propylthio, isopropylthio, butylthio, isobutylthio, tert-butylthio, pentylthio and hexylthio.

An aryl group means phenyl, naphthyl, indanyl and indenyl groups; an aryloxy group means phenyloxy, naphthyloxy, indanyloxy and indenyloxy groups; an aralkyl group means an ar-$C_{1-6}$ alkyl group, such as benzyl, diphenylmethyl, trityl and phenethyl groups; an arylthio group means phenylthio, naphthylthio, indanylthio and indenylthio groups.

An acyl group means a formyl group, a $C_{2-12}$ alkanoyl group such as acetyl, isovaleryl, propionyl and pivaloyl, an aralkylcarbonyl group such as benzylcarbonyl, and an aroyl group such as benzoyl and naphthoyl; an alkyloxycarbonyl group means, for example, a linear or branched chain $C_{1-12}$ alkyloxycarbonyl group, such as methoxycarbonyl, ethoxycarbonyl, 1,1-dimethylpropoxycarbonyl, isopropoxycarbonyl, 2-ethylhexyloxycarbonyl, tert-butoxycarbonyl and tert-pentyloxycarbonyl; an aralkyloxycarbonyl group means, for example, an ar-$C_{1-6}$ alkyloxycarbonyl groups, such as benzyloxycarbonyl and phenethyloxycarbonyl groups; an aryloxycarbonyl group means, for example, such a group as phenyloxycarbonyl; a heterocyclicoxycarbonyl group means, for example, such a group as 2-furfuryloxycarbonyl and 8-quinolyloxycarbonyl.

An alkylsulfonyl group means a $C_{1-12}$ alkylsulfonyl groups, such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl, heptylsulfonyl and octylsulfonyl; a lower alkylsulfonyl group means, for example, a $C_{1-6}$ alkylsulfonyl group, such as methylsulfonyl, ethylsulfonyl and propylsulfonyl; an arylsulfonyl group means such a group as phenylsulfonyl, p-toluenesulfonyl and naphthylsulfonyl.

An alkylamino group means a mono- or di-$C_{1-6}$ alkylamino group, such as methylamino, ethylamino, propylamino, isopropylamino, butylamino, dimethylamino, diethylamino, diisopropylamino and dibutylamino.

A heterocyclic group means a 5- or 6-membered fused or crosslinked heterocyclic group which contains at least one heteroatom selected from a nitrogen, oxygen or sulfur atom, such as pyrrolidinyl, piperidinyl, piperazinyl, homopiperazinyl, homopiperidinyl, morpholyl, thiomorpholyl, tetrahydroquinolinyl, tetrahydroisoquinolyl, quinuclidinyl, imidazolinyl, pyrrolyl, imidazolyl, pyrazolyl, pyridyl, pyrimidyl, quinolyl, quinolizinyl, thiazolyl, tetrazolyl, thiadiazolyl, pyrrolinyl, pyrazolinyl, pyrazolidinyl, purinyl, furyl, thienyl, benzothienyl, pyranyl, isobenzofuranyl, oxazolyl, isoxazolyl, benzofuranyl, indolyl, benzimidazolyl, benzoxazolyl, benzisoxazolyl, benzothiazolyl, quinoxalyl, dihydroquinoxalyl, 2,3-dihydrobenzothienyl, 2,3-dihydrobenzopyrrolyl, 2,3-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl, isoquinolyl, 1,3-benzodioxonyl and 1,4-benzodioxanyl groups.

An oxygen-containing heterocyclic group means, for example, such a group as 2-tetrahydropyranyl and 2-tetrahydrofuranyl; a sulfur-containing heterocyclic group means, for example, such a group as tetrahydrothiopyranyl; a substituted silyl group means, for example, such a group as trimethylsilyl, triethylsilyl, and tributylsilyl; an alkylsilylalkyl group means, for example, such a group as 2-(trimethylsilyl)ethyl.

An amino protective group comprises all groups that can be used as usual protective groups for an amino group, for example, such as those described in W. Greene, et. al., "Protective Groups in Organic Synthesis", 3rd edition, p. 494-615, 1999, John Wiley & Sons, Inc. Specifically, for example, included are an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkylsulfonyl group, an arylsulfonyl group and a substituted silyl group.

A hydroxyl protective group comprises all groups that can be used as usual protective groups for a hydroxyl group, for example, such as those described in W. Greene, et. al., "Protective Groups in Organic Synthesis", 3rd edition, p. 17-245, 1999, John Wiley & Sons, Inc. Specifically, for example, included are an acyl group, an alkyloxycarbonyl group, an aralkyloxycarbonyl group, a heterocyclicoxycarbonyl group, an alkyl group, an alkenyl group, an aralkyl group, an oxygen-containing heterocyclic group, a sulfur-containing heterocyclic group, an alkoxyalkyl group, an aralkyloxyalkyl group, an alkylsulfonyl group, an arylsulfonyl group and a substituted silyl group.

A carboxyl protective group comprises all groups that can be used as usual protective groups for a carboxyl group, for example, such as those described in W. Greene, et. al., "Protective Groups in Organic Synthesis", 3rd edition, p. 369-453, 1999, John Wiley & Sons, Inc. Specifically, for example, included are an alkyl group, an alkenyl group, an aryl group, an aralkyl group, an acylalkyl group, an arylthioalkyl group, an arylsulfonylalkyl group, an oxygen-containing heterocyclic group, an alkylsilylalkyl group, an acyloxyalkyl group, a nitrogen-containing heterocyclic alkyl group, a cycloalkyl group, an alkoxyalkyl group, an aralkyloxyalkyl group, an alkylthioalkyl group and a substituted silyl group.

Substituents for the alkyl group, the aryl group, the aralkyl group, the alkoxy group, the aryloxy group, the alkylthio group, the arylthio group, the alkenyl group, the alkenyloxy group, the amino group, the alkylsulfonyl group, the arylsulfonyl group, the carbamoyl group and the heterocyclic group in $R^1$ and $R^2$, and substituents for the alkylamino group in $R^3$, include groups selected from a halogen atom, a lower alkyl group, a cycloalkyl group, an aryl group, a lower alkoxy group, an aryloxy group, a lower alkylthio group, an arylthio group, a lower alkenyl group, a lower alkylsulfonyl group, an arylsulfonyl group, an alkylamino group, an optionally protected amino group, an optionally protected hydroxyl group an optionally protected carboxyl group, an acyl group and a heterocyclic group.

The salt of the compound of the general formula [1] includes a generally known salt formed at a basic group such as an amino group, or at an acidic group such as a hydroxyl or carboxyl group.

Salts formed at a basic group include, for example, salts with a mineral acid such as hydrochloric acid, hydrobromic acid, nitric acid and sulfuric acid; salts with an organic carboxylic acid such as formic acid, acetic acid, citric acid, oxalic acid, fumaric acid, maleic acid, succinic acid, malic acid, tartaric acid, aspartic acid, trichloroacetic acid and trifluoroacetic acid; and salts with a sulfonic acid such as methanesulfonic acid, benzenesulfonic acid, p-toluenesulfonic acid, mesitylenesulfonic acid and naphthalenesulfonic acid.

Salts formed at an acidic group include, for example, salts with an alkali metal such as sodium and potassium; salts with an alkaline-earth metal such as calcium and magnesium; an ammonium salt; and salts with a nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

Among the above-mentioned salts, preferable salts include pharmacologically acceptable salts.

When an isomer, for example, an optical isomer, a geometric isomer and a tautomer, exists in the alkyl ether derivative of the general formula [1] or a salt thereof, the present invention includes all those isomers and includes a hydrate, a solvate, and all crystal forms.

Preferably, the present alkyl ether derivative of the general formula [1] or the salt thereof includes the following compounds:

the compound in which $R^1$ is a hydrogen atom is preferred;
the compound in which $R^2$ is a hydrogen atom, a halogen atom, or an alkoxy group is preferred, and the compound in which $R^2$ is a hydrogen atom is more preferred;
the compound in which $R^3$ is a hydroxyl group is preferred;
the compound in which m is 2 is preferred;
the compound in which n is 2 or 3 is preferred, and the compound in which n is 3 is more preferred; and
further, the compound in which $R^1$ and $R^2$ is a hydrogen atom, $R^3$ is a hydroxyl group, m is 2 and n is 3 is most preferred.

Preferably, the alkyl ether derivative of the general formula [1] is 1-(3-(2-(1-benzothiophen-5-yl)ethoxy)propyl)azetidin-3-ol.

The present alkyl ether derivative of the general formula [1] or the salt thereof has a neurogenesis inducing effect, and the agent characterized in that it contains the alkyl ether derivative of the general formula [1] or the salt thereof is useful for the treatment and prevention of diseases in which neurogenesis is effective.

It has been known that a mental disorder therapeutic agent can be found based on the neurogenesis inducing effect in cultured neural stem cells (Patent Document 2). For example, valproic acid used as a therapeutic agent for bipolar disorder has been known to show the neurogenesis inducing effect in cultured neural stem cells (Proc. Natl. Acad. Sci. U.S.A., 2004, 101(47), pp. 16659-64).

Diseases in which neurogenesis induction is effective for the treatment or prevention include, for example, mental disorders and spinal cord injury. Preferable diseases include mental disorders.

The mental disorders in the present invention includes, for example, schizophrenia and its related diseases such as schizophrenia, schizotypal disorder, schizoaffective disorder and other nonorganic psychotic disorders; mood disorders such as manic episode, bipolar affective disorder (manic-depressive psychosis), depressive episode, recurrent depressive disorder and persistent mood disorders; and neurotic disorders such as phobic anxiety disorders, obsessive compulsive disorder and adjustment disorders, and preferably, schizophrenia, bipolar affective disorder (manic-depressive psychosis), depressive episode and recurrent depressive disorder.

The present alkyl ether derivative of the general formula [1] or the salt thereof used in the present invention can be produced by already known methods or their appropriate combination, or by the method described in the Patent Document 1.

The compound of the present invention can be formulated into pharmaceutical preparations such as oral agents (a tablet, a capsule, a powder, a granule, a fine powder, a pill, a suspension, an emulsion, a solution, a syrup, etc.), or injections, by adding thereto various types of pharmaceutical additives such as an excipient, a binder, a disintegrator, a disintegration inhibitor, an anticaking/antiadhesion agent, a lubricant, an absorption/adsorption carrier, a solvent, an extender, an isotonizing agent, a solubilizer, an emulsifier, a suspending agent, a thickener, a coating agent, an absorbefacient, a gelation/agglutination promoter, a light stabilizer, a preservative, an anti-moisture agent, an emulsion/suspension/dispersion stabilizer, a coloration preventing agent, a deoxidizer/antioxidant, correctives, a coloring agent, a whipping agent, an antifoaming agent, a soothing agent, an antistatic agent, or a buffer/pH adjuster.

The above-mentioned agents are formulated in the conventional manner.

Oral solid preparations such as a tablet, a powder, or a granule may be prepared according to common methods, using the following pharmaceutical additives for such solid preparations, for example: excipients such as lactose, sucrose, sodium chloride, glucose, starch, calcium carbonate, kaolin, crystalline cellulose, anhydrous dibasic calcium phosphate, partly pregelatinized starch, corn starch, or alginic acid; binders such as simple syrup, glucose solution, starch solution, gelatin solution, polyvinyl alcohol, polyvinyl ether, polyvinylpyrrolidone, carboxymethylcellulose, shellac, methylcellulose, ethylcellulose, sodium alginate, gum Arabic, hydroxypropylmethylcellulose, hydroxypropylcellulose, water, or ethanol; disintegrators such as dry starch, alginic acid, agar powders, starch, crosslinked polyvinylpyrrolidone, crosslinked carboxymethylcellulose sodium, carboxymethylcellulose calcium, or sodium starch glycolate; disintegration inhibitors such as stearyl alcohol, stearic acid, cacao butter, or hydrogenated oil; anticaking/antiadhesion agents such as aluminum silicate, calcium hydrogen phosphate, magnesium oxide, talc, or silicic acid anhydride; lubricants such as carnauba wax, light anhydrous silicic acid, aluminum silicate, magnesium silicate, hardened oil, hardened vegetable oil derivative, sesame oil, white beeswax, titanium oxide, dry aluminum hydroxide gel, stearic acid, calcium stearate, magnesium stearate, talc, calcium hydrogen phosphate, sodium lauryl sulfate, or polyethylene glycol; absorption promoters such as quaternary ammonium salts, sodium lauryl sulfate, urea, or enzyme; and absorption/adsorption carriers such as starch, lactose, kaolin, bentonite, silicic acid anhydride, hydrous silicon dioxide, magnesium aluminometasilicate, or colloidal silicic acid.

Moreover, as necessary, a tablet may be processed into a tablet coated with a common coating agent, such as a sugar-coated tablet, a gelatin-coated tablet, a gastric coated tablet, an enteric coated tablet, and a water-soluble film coated tablet.

A capsule is prepared by mixing the present compound with the aforementioned various types of pharmaceuticals and filling the obtained mixture in a hard gelatin capsule or soft capsule.

Furthermore, the compound of the present invention may also be formulated into water- or oil-type suspension, solution, syrup, and elixir, by common methods, using the aforementioned various types of additives for liquid preparations, such as a solvent, an extender, an isotonizing agent, a solubilizer, an emulsifier, a suspending agent, or a thickener.

An injection may be prepared by common methods, using pharmaceutical additives for liquid preparations including: diluents such as water, ethyl alcohol, Macrogol, propylene glycol, citric acid, acetic acid, phosphoric acid, lactic acid, sodium lactate, sulfuric acid, sodium hydroxide; pH adjusters and buffers, such as sodium citrate, sodium acetate, or sodium phosphate; stabilizers such as sodium pyrosulfite, ethylenediaminetetraacetic acid, thioglycolic acid, or thiolactic acid; isotonizing agents such as sodium chloride, glucose, mannitol, or glycerin; solubilizers such as carboxymethylcellulose sodium, propylene glycol, sodium benzoate, benzyl benzoate, urethane, ethanolamine, or glycerin; soothing agents such as calcium gluconate, chlorobutanol, glucose, or benzyl alcohol; and local anesthetics.

An eye drop may be prepared according to common methods by appropriately mixing the compound of the present invention with preservatives such as chlorobutanol, sodium dehydroacetate, benzalkonium chloride, cetyl pyridinium chloride, phenethyl alcohol, methyl parahydroxybenzoate, or benzethonium chloride; buffers such as borax, boric acid, or potassium dihydrogen phosphate; thickeners such as methylcellulose, hydroxyethylcellulose, carboxymethylcellulose, hydroxypropylmethylcellulose, polyvinyl alcohol, carboxymethylcellulose sodium, or chondroitin sulfate; solubilizers such as polysorbate 80 or polyoxyethylene hardened caster oil 60; stabilizers such as edetate sodium or sodium bisulfite; or isotonizing agents such as sodium chloride, potassium chloride, or glycerin.

A method for administration of the aforementioned preparations is not particularly limited. It is determined as appropriate, depending on the form of a preparation, the age of a patient, the sex thereof, and the degree of the symptoms of a patient, and other conditions.

The dosage of the active ingredient of the preparation of the present invention is selected as appropriate, depending on the usage, the age of a patient, the sex thereof, the form of disease, and other conditions. In general, the present preparation may be administered at a dosage between 1 and 1500 mg per adult per day, once or divided over several administrations, preferably may be administered at a dosage between 40 and 500 mg per adult per day, once or divided over several administrations.

EXAMPLES

Now, the present invention will be illustrated as a test example and formulation examples, which in no way limit the present invention.

To show its usefulness as a mental disorder therapeutic agent, the neurogenesis inducing effect of the compound of the present invention is demonstrated in cultured neural stem cells.

As a test substance, 1-(3-(2-(1-benzothiophen-5-yl)ethoxy)propyl)azetidin-3-ol (hereinafter, referred as T-817) maleate (hereinafter, referred as T-817MA) was used.

Test Example

Effect on Differentiation of Cultured Neural Stem Cell

Cultured neural stem cells were prepared according to the partially modified method of Hirabayashi (Development, 2004, 131(12), p. 2791-2801). The cerebrum was removed from an ICR mouse embryo (embryonic day 14) and incubated in artificial cerebrospinal fluid (124 mM NaCl, 5 mM KCl, 1.3 mM $MgCl_2$, 2 mM $CaCl_2$, 26 mM $NaHCO_3$, 10 mM D-Glucose, pH 7.4) containing 0.0625% trypsin and 0.1 mg/mL of DNaseI at 37° C. for 5 min. A trypsin inhibitor (final concentration: 0.35 mg/mL) was then added and the mixture was centrifuged at 800 rpm for 5 min. The obtained pellet was dispersed by pipetting in a neural stem cell culture medium (DMEM/F-12 culture medium containing 20 ng/mL basic fibroblast growth factor, 20 ng/mL epidermal growth factor and B27 supplement (Invitrogen)) to obtain single cell suspension. The obtained cell suspension was diluted to $1 \times 10^5$ cells/ml in 10 mL of the neural stem cell culture medium, and cultured for 7 days (using a 10-cm dish). On day 7 of culturing, the formed neurospheres were digested by trypsin and dispersed by pipetting as described above to obtain single cell suspension. The obtained isolated cells were cultured for further 7 days in the neural stem cell culture medium.

After 7 days of culturing, the formed neurospheres were digested by trypsin and dispersed by pipetting as described above to obtain single cell suspension. The cell suspension was diluted to $2 \times 10^5$ cells/mL in a culture medium (B27-supplemented DMEM/F-12 culture medium), then it was aliquoted by 100 µL/well to each well of a T-817MA treated group and a control group. To the well of the T-817MA treated group, 100 µL of T-817MA solution had been added (T-817MA was dissolved in B27 supplemented DMEM/F-12 culture medium to a final concentration of 10 µM). To the well of the control group, 100 µL of the B27-supplemented DMEM/F-12 culture medium had been added. As the culturing plate, a 0.5% polyethyleneimine-coated 48-well plate was used.

Both the T-817MA treated group and the control group were cultured for 3 days.

After 3 days of culturing, the cells were washed with phosphate-buffered saline (PBS), fixed with 4% paraformaldehyde/phosphate buffer, treated with 0.3% Triton X-100/PBS solution at room temperature for 5 minutes, washed with PBS, and incubated with 0.5% skim milk at room temperature for 1 hour. A mouse Tuj1 antibody (COVANCE), which had been 500 fold-diluted with 0.5% skim milk, was added, and the mixture was left at 4° C. overnight and then washed with PBS. Further, an Alexa Fluor 546-labelled anti-mouse IgG (Molecular Probes), which had been diluted by 1000-fold with PBS, was added to the cells, and the mixture was left at room temperature for 1 hour. The cells were washed with PBS and observed under fluorescence microscope, and the number of the Tuj1-positive cells emitting red fluorescence was counted, and its ratio against the total cell number was calculated as the differentiation ratio into neurons representing a neurogenesis inducing effect. The result is shown in Table 1.

TABLE 1

| | Control group | T-817MA treated group |
|---|---|---|
| Differentiation ratio into neurons (%) (Ratio of Tuj1 positive cells) | 13.0 | 27.4 |

As compared with the neural stem cells cultured in the B27 supplemented DMEM/F-12 culture media alone (control group), the cells cultured in the media containing T-817MA (10 μM) exhibited higher differentiation ratio, that is, a neurogenesis inducing effect of T-817MA.

Test Example 2

Antidepressive effect of T-817MA in the novelty-suppressed feeding test.
The novelty-suppressed feeding (NSF) test (Santarelli et al., 2003, Science. 301: 805-9) was performed to assess antidepressant efficacy of T-817MA. Male DBA/2J mice (7 weeks old, 20-21 animals/group) were used. We administrated mice orally with T-817MA (10 mg/kg), or vehicle (distilled water) for 28 days before NSF test. At the time of testing, mice that had been food deprived for 24 hours were gently placed in a corner of a brightly lit arena (approximately 650 lux at floor of arena, 50×50×20 cm) for a maximum of 5 minutes. The floor was covered with approximately 2 cm of bedding. Pellet of food was attached by wire at the center of the arena. When the mouse was observed to be sitting on its haunches eating food with its forepaws, the latency to feed was recorded. In the NSF test, the group treated with T-817MA (10 mg/kg) resulted in significant decreased latency to feed (P<0.01). Statistical differences between vehicle group and T-817MA treated group were found by Dunnett test. The result is shown in Table 2.

TABLE 2

| Group | T-817MA 10 mg/kg | Vehicle |
|---|---|---|
| NSF latency (mean) (sec) | 145.5 | 227.2 |

Formulation Example 1

A mixture of 50 mg of T-817MA, 20 mg of lactose, 25 mg of corn starch and 40 mg of Avicel PH101 (Asahi Kasei Corporation) was kneaded with 5% polyvinylpyrrolidone K30 aqueous solution, dried at 60° C., mixed with a mixture of 10 mg of Kollidon CL (BASF), 10 mg of Avicel PH302 (Asahi Kasei Corporation), 18 mg of light anhydrous silicic acid and 2 mg of magnesium stearate, compressed to give a round-shaped tablet of 7 mm diameter and 75 mg weight, containing 50 mg of T-817MA.

Formulation Example 2

A mixture of 50 mg of T-817MA, 20 mg of lactose and 53 mg of corn starch was kneaded with 5% polyvinylpyrrolidone K30 aqueous solution, dried at 60° C., mixed with a mixture of 7 mg of Kollidon CL (BASF), 18 mg of Avicel PH302 (Asahi Kasei Corporation) and 2 mg of magnesium stearate, then 150 mg of which per capsule was filled in a No. 4 gelatin capsule to make up a capsule.

INDUSTRIAL APPLICABILITY

The alkyl ether derivative or the salt thereof of the present invention shows a neurogenesis inducing effect and is useful as a neurogenesis inducer and a mental disorder therapeutic agent.

The invention claimed is:

1. A method of inducing neurogenesis comprising:
administering to a subject in need thereof a benzothiophene alkyl ether derivative represented by formula:

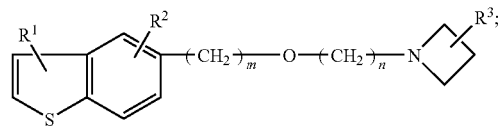

wherein, $R^1$ and $R^2$, which are identical or different, represent one or more groups selected from a hydrogen atom, a halogen atom, an optionally substituted alkyl, aryl, aralkyl, alkoxy, aryloxy, alkylthio, arylthio, alkenyl, alkenyloxy, amino, alkylsulfonyl, arylsulfonyl, carbamoyl or heterocyclic group, an optionally protected amino, hydroxyl or carboxyl group, a nitro group and an oxo group;
$R^3$ represents an optionally substituted alkylamino group or an optionally protected amino or hydroxyl group; and
m and n, which are identical or different, represent an integer from 1 to 6; or a salt thereof.

2. The method according to claim 1, wherein in said benzothiophene alkyl ether derivative or salt thereof $R^1$ is a hydrogen atom and $R^2$ is a hydrogen atom, a halogen atom or an alkoxy group.

3. The method according to claim 1, wherein in said benzothiophene alkyl ether derivative or salt thereof m is 2 and n is 2 or 3.

4. The method according to claim 1, wherein in said benzothiophene alkyl ether derivative or salt thereof $R^2$ is a hydrogen atom, $R^3$ is a hydroxyl group and n is 3.

5. The method according to claim 1, wherein the benzothiophene alkyl ether derivative is 1-(3-(2-(1-benzothiophen-5-yl)ethoxy)propyl)azetidin-3-ol or a salt thereof.

6. A method for treating a mental disorder by inducing neurogenisis comprising:
   administering to a subject in need thereof a benzothiophene alkyl ether derivative represented by formula:

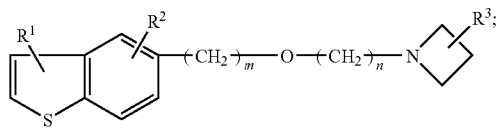

wherein, $R^1$ and $R^2$, which are identical or different, represent one or more groups selected from a hydrogen atom, a halogen atom, an optionally substituted alkyl, aryl, aralkyl, alkoxy, aryloxy, alkylthio, arylthio, alkenyl, alkenyloxy, amino, alkylsulfonyl, arylsulfonyl, carbamoyl or heterocyclic group, an optionally protected amino, hydroxyl or carboxyl group, a nitro group and an oxo group;
   $R^3$ represents an optionally substituted alkylamino group or an optionally protected amino or hydroxyl group; and
   m and n, which are identical or different, represent integer from 1 to 6; or a salt thereof.

7. The method according to claim 6, wherein in said benzothiophene alkyl ether derivative or salt thereof $R^1$ is a hydrogen atom and $R^2$ is a hydrogen atom, a halogen atom or an alkoxy group.

8. The method according to claim 6, wherein in said benzothiophene alkyl ether derivative or salt thereof m is 2 and n is 2 or 3.

9. The method according to claim 6, wherein in said benzothiophene alkyl ether derivative or salt thereof $R^2$ is a hydrogen atom, $R^3$ is a hydroxyl group and n is 3.

10. The method according to claim 6, wherein the benzothiophene alkyl ether derivative is 1-(3-(2-(1-benzothiophen-5-yl)ethoxy)propyl)azetidin-3-ol or a salt thereof.

11. The method according to claim 6, wherein the mental disorder is schizophrenia and its related diseases.

12. The method according to claim 6, wherein said mental disorder is mood disorder.

13. The method of claim 6, wherein said mental disorder is neurotic disorder.

14. The method of claim 1, wherein said benzothiophene alkyl ether derivative or salt thereof is administered orally.

15. The method of claim 6, wherein said benzothiophene alkyl ether derivative or salt thereof is administered orally.

16. The method of claim 1, wherein said benzothiophene alkyl ether derivative or salt thereof is administered by injection.

17. The method of claim 6, wherein said benzothiophene alkyl ether derivative or salt thereof is administered by injection.

18. The method of claim 1, wherein said benzothiophene alkyl ether derivative or salt thereof is administered by eye drop.

19. The method of claim 6, wherein said benzothiophene alkyl ether derivative or salt thereof is administered eye drop.

* * * * *